# United States Patent
Celewicz et al.

(10) Patent No.: US 9,388,209 B2
(45) Date of Patent: Jul. 12, 2016

(54) 2',3'-DIDEOXY-5-FLUOROURIDINE DERIVATIVES, A PROCESS FOR THE MANUFACTURE THEREOF AND APPLICATION THEREOF

(71) Applicant: ADAM MICKIEWICZ UNIVERSITY, Poznan (PL)

(72) Inventors: Lech Celewicz, Poznanń (PL); Karol Kacprzak, Pecna (PL); Dagmara Baraniak, Jarocin (PL); Marta Lewandowska, Śrem (PL); Piotr Ruszkowski, Suchy Las (PL)

(73) Assignee: ADAM MICKIEWICZ UNIVERSITY, Poznań (PL)

( * ) Notice: Subject to any disclaimer, the term of this patent is extended or adjusted under 35 U.S.C. 154(b) by 65 days.

(21) Appl. No.: 14/413,560

(22) PCT Filed: Mar. 4, 2014

(86) PCT No.: PCT/PL2014/050009
§ 371 (c)(1),
(2) Date: Jan. 8, 2015

(87) PCT Pub. No.: WO2015/050467
PCT Pub. Date: Apr. 9, 2015

(65) Prior Publication Data
US 2016/0152655 A1 Jun. 2, 2016

(30) Foreign Application Priority Data
Feb. 12, 2014 (PL) ..................................... P.407152

(51) Int. Cl.
| | | |
|---|---|---|
| *A61K 31/513* | (2006.01) | |
| *A61K 31/7072* | (2006.01) | |
| *C07H 19/073* | (2006.01) | |
| *C07D 453/04* | (2006.01) | |
| *C07H 19/06* | (2006.01) | |

(52) U.S. Cl.
CPC .............. *C07H 19/06* (2013.01); *A61K 31/513* (2013.01); *A61K 31/7072* (2013.01); *C07D 453/04* (2013.01); *C07H 19/073* (2013.01)

(58) Field of Classification Search
None
See application file for complete search history.

(56) References Cited

FOREIGN PATENT DOCUMENTS

EP 1 477 488 B1 8/2009

OTHER PUBLICATIONS

Lewandowska et al., "Synthesis of 3'-azido-2',3'-dideoxy-5-fluorouridine phosphoramidates and evaluation of their anticancer activity" European Journal of Medicinal Chemistry (2013) vol. 67 pp. 188-195.*
Colla et al., "Synthesis and biological activity of 3'-azido- and 3'-amino substituted nucleotide analogs", *Eur. J. Med. Chem.*, 1985, 20, 4, 295-301.
Lin et al., "Synthesis and Biological Activity of Various 3'Azido and 3'-Amino Analogues of 5-Substituted Pyrimidine Deoxyribonucleosides", *J. Med. Chem.*, 1983, 26, 1691-1696.
Vichai et al., "Sulforhodamine B colorimetric assay for cytotoxicity screening", *Nature Protocols*, 2006, 1,3, 1112-1116.
Grabowski et al., "Properties and Architecture of Drugs and Natural Products Revisited", *Curr. Chem. Biol.*, 2007, 1, 115-127.
Vistoli et al., "Assessing drug-likeness—what are we missing?", *Drug Discov. Today* 2008, 13, 7/8, 285-294.
Mauri et al., "Dragon Software: An Easy Approach to Molecular Descriptor Calculations", *MATCH Commun. Math. Comput. Chem.*, 2006, 56, 237-248.
Kacprzak et al., "An Improved Synthesis of 10,11-Didehydro *Cinchona* Alkaloids", Chirality, 2008, 20, 441-445.
Baraniak et al., "Synthesis of 3'azido-3'deoxythymidine (AZT)-*Cinchona* alkaloid conjugates via click chemistry: Toward novel fluorescent markers and cytostatic agents", *Bioorganic & Medicinal Chem. Letters*, 2011, 21, 2, 723-726.
Kumar et al., "Phenyl 1,2,3-Triazole-Thymidine Ligands Stabilize G-Quadruplex DNA, Inhibit DNA Synthesis and Potentially Reduce Tumor Cell Proliferation over 3'-Azido Deoxythymidine", PLOS ONE, 2013, 8, 8, e70798, 1-12.
Wei et al., "Design, Synthesis, and in Vitro and in Vivo Biological Studies of a 3'-Deoxythymidine Conjugate that Potentially Kills Cancer Cells Selectively", PLOS ONE, 2012, 7, 12, e52199, 1-8.
Lin et al., "A Novel Synthesis and Biological Activity of Several 5-Halo-5'-amino Analogues of Deoxyribopyrimidine Nucleosides", *J. Med. Chem.*, 1978, 21, 1, 106-109.
Jarrahpour et al., "Petra, Osiris and Molinspiration (POM) together as a successful support in drug design: antibacterial activity and biopharmaceutical characterization of some azo Schiff bases", *Med. Chem. Res.*, 2012, 21, 1984-1990.

(Continued)

Primary Examiner — Eric Olson
(74) Attorney, Agent, or Firm — Oliff PLC

(57) ABSTRACT

2',3'-dideoxy-5-fluorouridine derivatives have general formula 1:

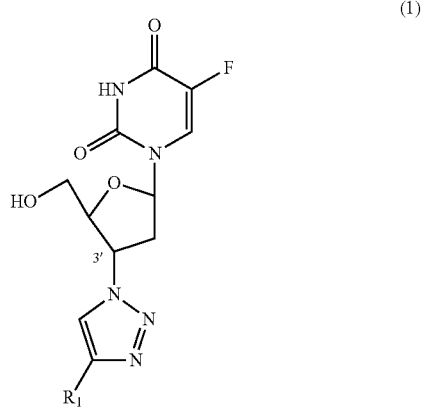

wherein:
R₁ denotes *cinchona* alkaloid fragment with defined absolute configuration at C-8 and C-9 atoms. A process for the manufacture of 2',3'-dideoxy-5-fluorouridine derivatives of general formula 1 and application of 2',3'-dideoxy-5-fluorouridine derivatives of general formula 1 in the anticancer treatment of breast cancer, cervical cancer and hepatic cancer are also indicated.

11 Claims, No Drawings

(56) References Cited

OTHER PUBLICATIONS

U.S. Appl. No. 14/413,618, filed Jan. 8, 2015 in the name of Celewicz et al.
International Search Report issued on May 13, 2014 in International Application No. PCT/PL2014/050009.
Written Opinion of the International Searching Authority issued on May 13, 2014 in International Application No. PCT/PL2014/050009.
International Search Report issued on May 23, 2014 in International Application No. PCT/PL2014/050010.
Written Opinion of the International Searching Authority issued on May 23, 2014 in International Application No. PCT/PL2014/050010.

* cited by examiner

2',3'-DIDEOXY-5-FLUOROURIDINE DERIVATIVES, A PROCESS FOR THE MANUFACTURE THEREOF AND APPLICATION THEREOF

The subject matter of the invention is novel 2',3'-dideoxy-5-fluorouridine derivatives, a process for the manufacture thereof and also their application as cytotoxic agents.

Cancer diseases are one of the principal health disorders reported in humans, having the highest mortality rates and increasing numbers of new cases, primarily related to the increased life length and to lifestyle. The treatment of cancer discuses is difficult, expensive and in many cases not efficacious. Therefore, there is an urgent need for novel substances with cytostatic activity. They may be to sourced from natural products and their derivatives as well as constitute synthetic compounds.

Derivatives or analogues of purine or pyrimidine bases and modified nucleosides are a very important group of synthetic cytostatic agents. These include compounds, such as 5-fluorouracil and its prodrugs, e.g. 5-fluoro-2'-deoxyuridine (floxuridine). Both 5-fluorouracil and 5-fluoro-2'-deoxyuridine have similar cytostatic activity, being used in the treatment of cancer, such as breast cancer, gastric cancer, colorectal cancer, ovarian cancer and the like, either in monotherapy or combined with each other or with other anticancer agents. 5-Fluoro-2'-deoxyuridine is also used in the treatment of hepatic cancer owing better hepatic metabolism compared to 5-fluorouracil. Difficulties with the use of 5-fluorouracil and 5-fluoro-2'-deoxyuridine in therapy are related to the development of cancer cell resistance toward those agents due to their long-term intake. Another significant limitation is relatively high toxicity of 5-fluorouracil responsible for neurotoxic and cardiotoxic effects. Furthermore, as those agents are net selective with respect to cancerous and normal cells, their application in therapy is considerably limited. Another major issue is low bioavailability of 5-fluoro-2'-deoxyuridine related to its highly negative partition coefficient (log $P=-1.72$); therefore, the agent is excessively polar to cross lipid cell membranes, being administered by intravenous infusion.

Attempts have been made to solve those problems through modifications of 5-fluoro-2'-deoxyuridine, such as by changing the substituent at position 3'. An amino group and fluorine, chlorine, bromine and iodine were reported to reduce cytostatic activity. An azide group-containing derivative (3'-azido-2',3'-dideoxy-5-fluorouridine (AddFU)) in turn proves to have weak activity ($IC_{50}$ 34 µg/mL) (Colla L., Herdewijn P., De Clereq E., Balzarini J., Vanderhaeghe H., *Eur. J. Med. Chem.* 1985, 20, 295) against L1210 cancer in mice induced by MLV retroviruses and against sarcoma 180 in vitro (Lin T.-S., Gao Y.-S., Mancini W. R., *J. Med. Chem.* 1983, 26, 1691).

The objective of the present invention was to develop novel cytotoxic compounds, being 5-fluoro-2'-deoxyuridine derivatives with activity higher than or comparable to the known and already used 5-fluoro-2'-deoxyuridine and 3'-azido-2',3'-dideoxy-5-fluorouridine (AddFU).

The subject matter of the invention is 2',3'-dideoxy-5-fluorouridine derivatives of general formula 1.

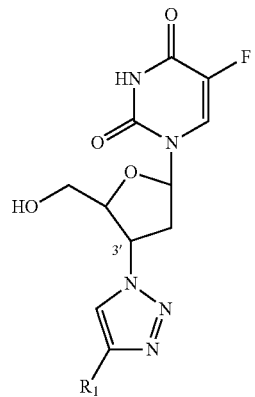

wherein:
$R_1$ denotes a fragment of *cinchona* alkaloid of natural origin obtained from bark or other parts of *Cinchona* species plants or synthetic of general formula 2 or 3 and with defined absolute configuration at C-8 and C-9 atoms which includes all four possible diastereomeric forms, that is (8R,9S) or (8S,9R) or (8R,9R) or (8S,9S). Common numbering used in *cinchona* alkaloid chemistry was used to define the absolute configuration.

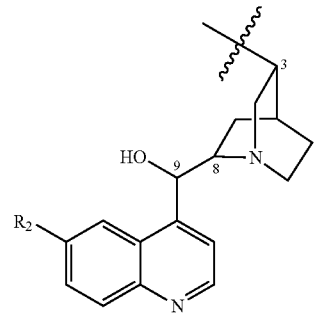

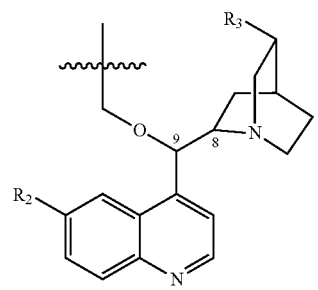

wherein:
$R_2$ denotes hydroxy group, H or an alkoxy group containing between 1 and 12 C atoms in a straight or branched chain or a cycloalkyl substituent containing between 3 and 10 C atoms, preferably methoxy group.

$R_3$ denotes vinyl, ethyl or acetylene group.

In the second aspect the subject matter of the invention is salts of 2',3'-dideoxy-5-fluorouridine derivatives:
monosalts of general formula 4 and 5
disalts of general formula 6, wherein a double protonated alkaloid fragment is the dication.

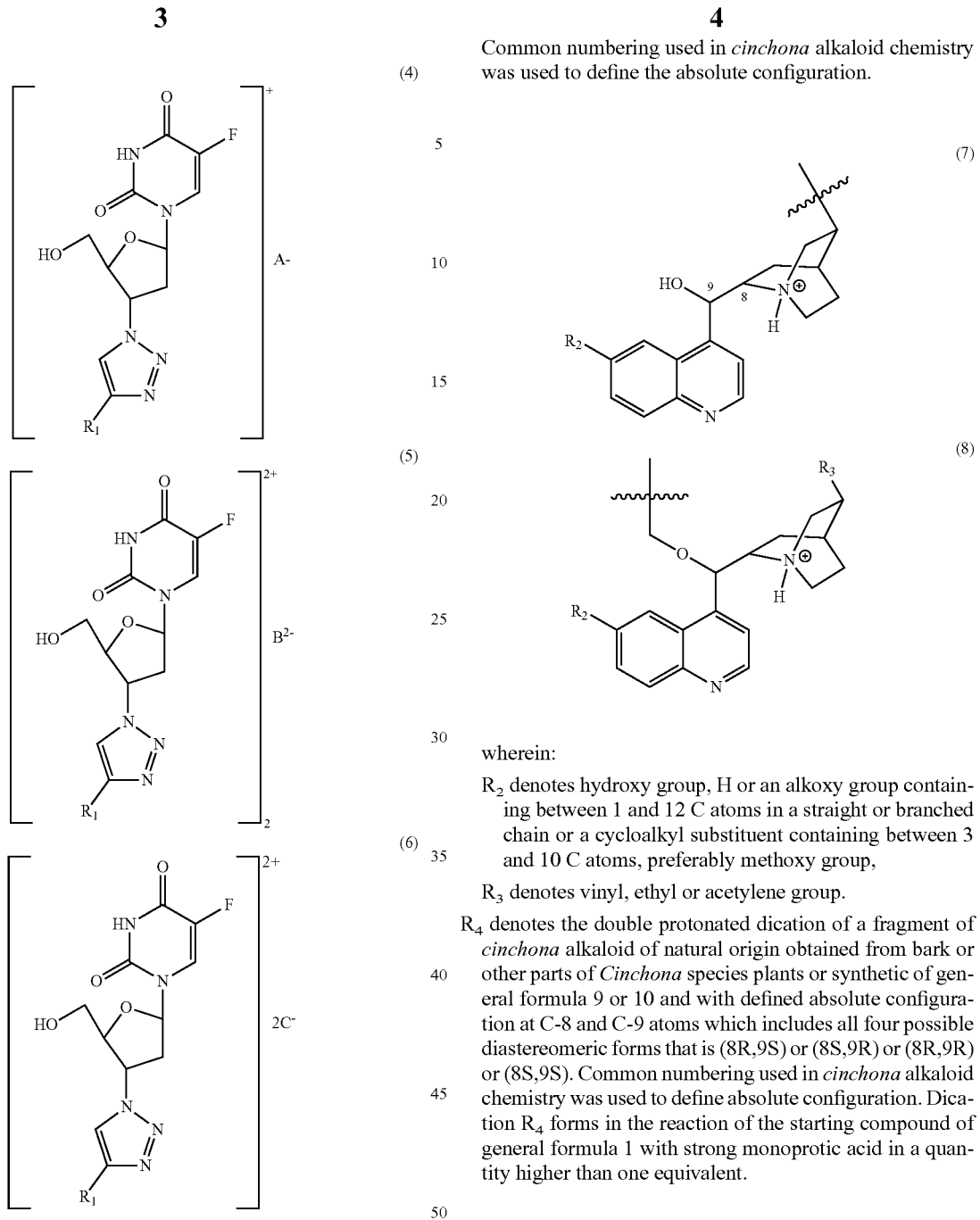

wherein:
A⁻ denotes Cl⁻, Br⁻, I⁻, $NO_3^-$, $HCOO^-$, $CH_3COO^-$, $CH_3SO_3^-$, $CH_3C_6H_4SO_3^-$, $CH_3CH(OH)COO^-$, $HOOC(CHOH)_2COO^-$, $HOOC(CH_2)_2COO^-$, cis-$C_4H_3O_4^-$, trans-$C_4H_3O_4^-$, $HOCH_2(CHOH)_4COO^-$, $C_6H_8O_6^-$, $C_6H_7O_7^-$ $B^{2-}$ denotes $SO_4^{2-}$, $HPO_4^{2-}$, $^-OOC(CH_2)_2COO^-$, $^-OOC(CHOH)_2COO^-$, cis-$C_4H_2O_4^{2-}$, trans-$C_4H_2O_4^{2-}$ C⁻ denotes Cl⁻, Br⁻, I⁻, $NO_3^-$, $CH_3SO_3^-$.

$R^1$ denotes the monocation of a fragment of *cinchona* alkaloid of natural origin obtained from bark or other parts of *Cinchona* species plants or synthetic of general formula 7 or 8 and with defined absolute configuration at C-8 and C-9 atoms which includes all four possible diastereomeric forms, that is (8R,9S) or (8S,9R) or (8R,9R) or (8S,9S).

Common numbering used in *cinchona* alkaloid chemistry was used to define the absolute configuration.

wherein:
$R_2$ denotes hydroxy group, H or an alkoxy group containing between 1 and 12 C atoms in a straight or branched chain or a cycloalkyl substituent containing between 3 and 10 C atoms, preferably methoxy group, $R_3$ denotes vinyl, ethyl or acetylene group.

$R_4$ denotes the double protonated dication of a fragment of *cinchona* alkaloid of natural origin obtained from bark or other parts of *Cinchona* species plants or synthetic of general formula 9 or 10 and with defined absolute configuration at C-8 and C-9 atoms which includes all four possible diastereomeric forms that is (8R,9S) or (8S,9R) or (8R,9R) or (8S,9S). Common numbering used in *cinchona* alkaloid chemistry was used to define absolute configuration. Dication $R_4$ forms in the reaction of the starting compound of general formula 1 with strong monoprotic acid in a quantity higher than one equivalent.

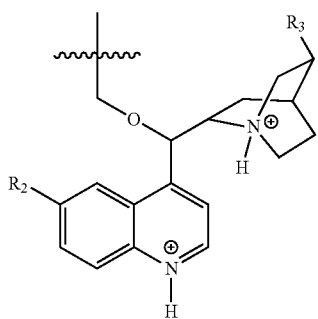

(10)

wherein:

R$_2$ and R$_3$ are as defined above.

In the third aspect, the subject matter of the invention is the process for the manufacture of 2',3'-dideoxy-5-fluorouridine derivatives of general formula 1, wherein R$_1$, R$_2$ and R$_3$ are as defined hereinabove, involving copper(I)-catalysed 1,3-dipolar Huisgen cycle-addition between 3'-azido-2',3'-dideoxy-5-fluorouridine (AddFU) of general formula 11.

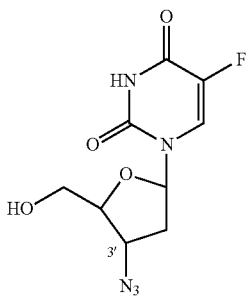

(11)

and an appropriate alkyne derivative of *cinchona* alkaloid of general formula 12 or 13,

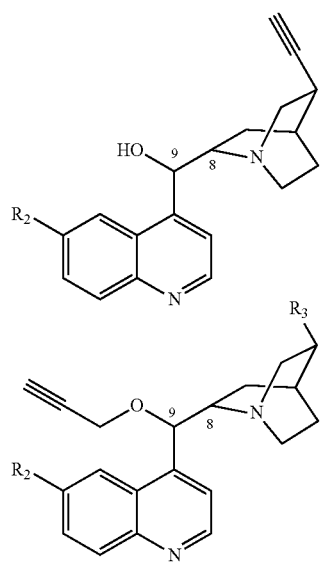

(12)

(13)

wherein R$_2$ and R$_3$ are as defined hereinabove.

Table 1 shows examples of the compounds of the invention and appropriate alkyne derivatives of *cinchona* alkaloids of formula 12 or 13, used in the synthesis of respective compounds.

The reaction proceeds at any ratio of the azide and the alkaloid alkyne derivative; however, considering the yield of synthesis, an equimolar ratio between the reagents is preferable. The reaction is carried out in aqueous-organic mixtures with a water content from 1% to 99% and a water-miscible organic solvents selected from the group of lower aliphatic alcohols, aliphatic ketones, cyclic ethers or aliphatic nitriles. Methanol, ethanol, tert-butanol, dioxane, acetone or acetonitrile are preferably used, and the reaction is carried out most preferably in a dioxane-water or methanol-water mixture at a solvent volume ratio of 1:1. The reaction proceeds in a wide range of temperatures between 0° C. and 90° C.; due to practical reasons, however, the reaction is preferably carried out at room temperature.

The reaction is catalysed by Cu(I) ions which may be added directly as copper(I) salts, most preferably in the form of copper(I) iodide, or generated directly in the reaction medium. More preferably, the Cu(I) ions which catalyse the reaction are formed in situ in the reaction mixture by reducing Cu(II) ions of any soluble copper(II) salt, preferably copper (II) sulphate pentahydrate, and an inorganic reducing agent, in particular water-soluble sulphites, metallic copper or an organic reducing agent, in particular hydroxylamine, hydroquinone or, most preferably, sodium ascorbate. In a direct synthesis with the use of copper(I) salts as the catalyst, it is used in a quantity of between 0.01 and 1.0 equivalent of Cu(I) ions with respect to 3'-azido-2',3'-dideoxy-5-fluorouridine. In a second variant where the required copper(I) ions are formed in situ, a copper(II) salt is used in a quantity of between 0.01 and 1.0 equivalent of copper(II) ions with respect to 3'-azido-2',3'-dideoxy-5-fluorouridine, preferably 0.75 equivalent of copper(II) sulphate and between 0.01 and 1.0 equivalent of the reducing agent, preferably an organic reducing agent, with respect to 3'-azido-2',3'-dideoxy-5-fluorouridine, most preferably sodium ascorbate in a quantity of 0.75 equivalent. In the variant of synthesis using Cu(I) ions formed in situ, it is most preferable to use the same or larger amount of sodium ascorbate with respect to the copper(II) salt due to the instability of copper(I) ions and their oxidation by oxygen to catalytically inactive copper(II) salts.

The resulting product is isolated from the reaction mixture by being removed from the solvent mixture and purified using column chromatography on silica gel, preferably using chloroform followed by a chloroform-methanol mixture containing between 1% and 50% by volume of methanol, most preferably 20% as the mobile phase.

Monosalts of 2',3'-dideoxy-5-fluorouridine derivatives of general formula 4 are obtained in a reaction between a compound of general formula 1 and no more than an equimolar quantity of a respective inorganic or organic acid.

Monosalts of general formula 5 are obtained in a reaction between a compound of general formula 1 and no more than a half equivalent of a respective diprotic inorganic or organic acid.

Disalts of general formula 6 are obtained in a reaction between one equivalent of a compound of general formula 1 and more than one equivalent of a respective monoprotic acid; preferably, two equivalents of the acid are used. When one to two equivalents of the acid are used, a mixture of mono- and disalts is obtained.

Preparations of the salts of general formulas 4, 5 or 6 are carried out in polar solvents, such as: aliphatic alcohols containing from 1 to 3 carbon atoms in the chain, DMF, DMSO, acetonitrile or mixtures thereof with water in a quantity of from 1 to 90% (v/v), preferably in a quantity of 50% water, still most preferably in methanol or ethanol.

The resulting salts are isolated by removing the solvent in a vacuum evaporator or by slow crystallisation.

TABLE 1

| No. | Formula | Abbreviated name | Name | Absolute configuration at C8 and C9 atoms in the product | Alkaloid substrate for synthesis |
|---|---|---|---|---|---|
| 1. | 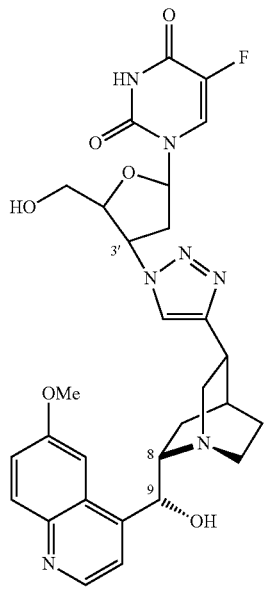 | QN5FdU | 5-Fluoro-1-[4-(4-{6-[hydroxy-(6-methoxyquinolin-4-yl)-methyl]-1-azabicyclo[2.2.2]oct-3-yl}-[1,2,3]triazol-1-yl)-5-hydroxymethyl-tetrahydro-furan-2-yl]-1H-pyrimidine-2,4-dione | (8S,9R) | (8S,9R)-10,11-didehydro-quinine |
| 2. | 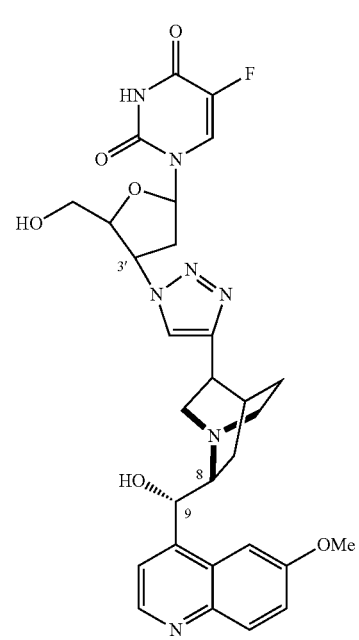 | QD5FdU | 5-Fluoro-1-[4-(4-{6-[hydroxy-(6-methoxyquinolin-4-yl)-methyl]-1-azabicyclo[2.2.2]oct-3-yl}-[1,2,3]triazol-1-yl)-5-hydroxymethyl-tetrahydro-furan-2-yl]-1H-pyrimidine-2,4-dione | (8R,9S) | (8R,9S)-10,11-didehydro-quinidine |

TABLE 1-continued

| No. | Formula | Abbreviated name | Name | Absolute configuration at C8 and C9 atoms in the product | Alkaloid substrate for synthesis |
|---|---|---|---|---|---|
| 3. | | CD5FdU | 5-Fluoro-1-(5-hydroxymethyl-4-{4-[6-(hydroxy-quinolin-4-yl-methyl)-1-aza-bicyclo[2.2.2]oct-3-yl]-[1,2,3]triazol-1-yl}-tetrahydro-furan-2-yl)-1H-pyrimidine-2,4-dione | (8S,9R) | (8R,9S)-10,11-didehydro-cinchonidine |
| 4. | | CN5FdU | 5-Fluoro-1-(5-hydroxymethyl-4-{4-[6-(hydroxy-quinolin-4-yl-methyl)-1-aza-bicyclo[2.2.2]oct-3-yl]-[1,2,3]triazol-1-yl}-tetrahydro-furan-2-yl)-1H-pyrimidine-2,4-dione | (8R,9S) | (8R,9S)-10,11-didehydro-cinchonine |

TABLE 1-continued

| No. | Formula | Abbreviated name | Name | Absolute configuration at C8 and C9 atoms in the product | Alkaloid substrate for synthesis |
|---|---|---|---|---|---|
| 5. | 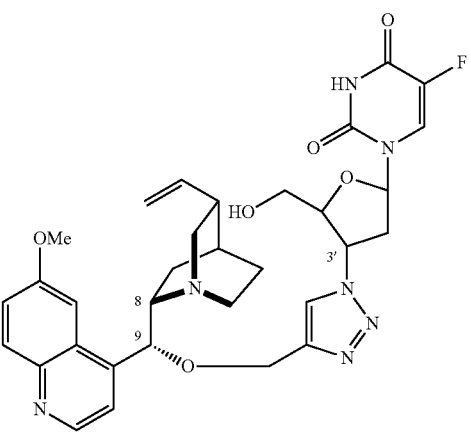 [SMILES: C=CC1C[N@@]2CCC1C[C@H]2[C@H](OCc1cn(C2CC(n3cc(F)c(=O)[nH]c3=O)OC2CO)nn1)c1ccnc2ccc(OC)cc12] | PQN5FdU | 5-Fluoro-1-(5-hydroxymethyl-4-{4-[(6-methoxyquinolin-4-yl)-(5-vinyl-1-aza-bicyclo[2.2.2]oct-2-yl)-methoxymethyl]-[1,2,3]triazol-1-yl}-tetrahydrofuran-2-yl)-1H-pyrimidine-2,4-dione | (8S,9R) | (8S,9R)-9-O-propargyl-quinine |
| 6. | 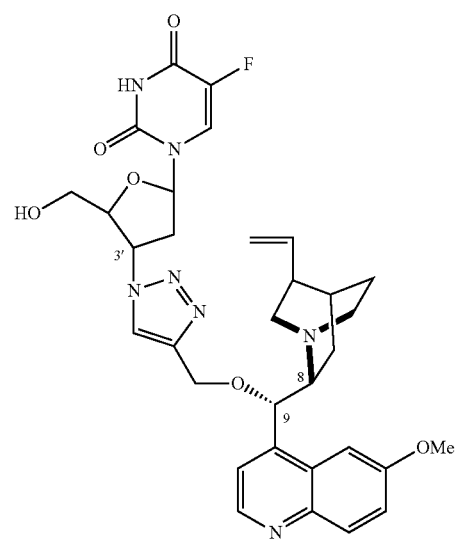 | PQD5FdU | 5-Fluoro-1-(5-hydroxymethyl-4-{4-[(6-methoxyquinolin-4-yl)-(5-vinyl-1-aza-bicyclo[2.2.2]oct-2-yl)-methoxymethyl]-[1,2,3]triazol-1-yl}-tetrahydrofuran-2-yl)-1H-pyrimidine-2,4-dione | (8R,9S) | (8R,9S)-9-O-propargyl-quinidine |
| 7. | 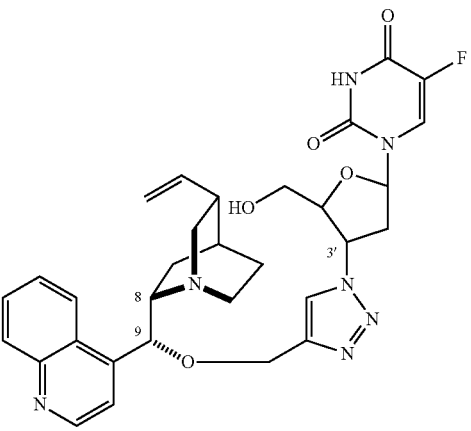 [SMILES: C=CC1C[N@@]2CCC1C[C@H]2[C@H](OCc1cn(C2CC(n3cc(F)c(=O)[nH]c3=O)OC2CO)nn1)c1ccnc2ccccc12] | PCD5FdU | 5-Fluoro-1-(5-hydroxymethyl-4-{4-[quinolin-4-yl-(5-vinyl-1-aza-bicyclo[2.2.2]oct-2-yl)-methoxymethyl]-[1,2,3]triazol-1-yl}-tetrahydrofuran-2-yl)-1H-pyrimidine-2,4-dione | (8S,9R) | (8S,9R)-9-O-propargyl-cinchonidine |

TABLE 1-continued

| No. | Formula | Abbreviated name | Name | Absolute configuration at C8 and C9 atoms in the product | Alkaloid substrate for synthesis |
|---|---|---|---|---|---|
| 8. |  | PCN5FdU | 5-Fluoro-1-(5-hydroxymethyl-4-{4-[quinolin-4-yl-(5-vinyl-1-azabicyclo[2.2.2]oct-2-yl)-methoxymethyl]-[1,2,3]triazol-1-yl}-tetrahydrofuran-2-yl)-1H-pyrimidine-2,4-dione | (8R,9S) | (8R,9S)-9-O-propargyl-cinchonine |

In the fourth aspect, the subject matter of the invention is an application of 2',3'-dideoxy-5-fluorouridine derivatives of general formula 1 and their pharmaceutically acceptable salts of the invention in the anticancer treatment of breast cancer, cervical cancer and hepatic cancer. In vitro studies on cancer cell lines of breast cancer, cervical cancer and hepatic cancer confirmed cytotoxic action with activity higher than the activity of 2'-deoxy-5-fluorouridine (5FdU) and 3'-azido-2',3'-dideoxy-5-fluorouridine (AddFU) when used under identical conditions.

Cytotoxic activity tests were performed using the following cancer cell lines: MCF-7 (breast cancer), HeLa (cervical cancer) and Hep-G2 (hepatic cancer) obtained from ECACC (European Collection of Cell Cultures).

Cytotoxicity tests were carried out using a standard procedure with sulphorhodamine B. They involved incubation of the cancer cell lines in the logarithmic growth phase for 72 hours with the compound tested and, subsequently, spectrophotometric determination of the degree of cell growth inhibition using adsorption of a dye (sulphorhodamine B) which binds cellular proteins. The determination was carried out according to a procedure reported in: Vichai, V., Kirtikara, K. *Nature Protocols,* 2006, 1, 1112.

Determination of Cytotoxicity
Preparation of Cells For the Experiment:

Cells of the cell line tested in the logarithmic growth phase were seeded onto 24-well plates in a quantity of 20,000 cells/2 mL of the growth medium per well and, subsequently, incubated in an incubator at 37° C., in the 5% $CO_2$ atmosphere for 24 hours.

Preparation of Test Compound Solutions:

Solutions of the test compounds were prepared in DMSO in the following concentration range: 0.05; 0.1; 0.5; 1; 5; 10; 50; 100; 500 μM.

The cells of the lines tested were treated with the solutions of the test compounds in a laminar-flow chamber which ensured sterile working conditions according to the following procedure: the first three wells were used as a blank: they contained 20 μL of DMSO only; successive solutions of the test compound were added to subsequent wells (20 μL), starting with the lowest concentration (three wells for each concentration level). Subsequently, the plates were placed in an incubator for 72 hours.

After the end of incubation, the adhered cells were fixed by adding 500 μL of cold (4° C. 50% trichloroacetic acid (TCA) and incubated at 4° C. for 1 hour. Subsequently, each well was rinsed with sterile water and dried. The operation was repeated five times. The fixed cells were stained for 30 minutes by adding 500 μL of 0.4% of a dye solution (sulphorhodamine B) dissolved in 1% acetic acid. Any unbound dye was removed by decanting it from the plate, and the cells were washed 4 times with 1% acetic acid. Subsequently, the plates were dried in air for approx. 5 minutes. Any unbound dye was dissolved by adding 1500 μL of 10 mM Tris-base buffer (trishydroxymethylaminomethane) to each well and shaken using an orbital shaker for 5 minutes. Subsequently, 200 μL of solution from each well was transferred to each of two wells on a new 96-well plate and absorption of the solutions was determined spectrophotometrically at a wavelength of 490-530 nm using a plate reader. Percentage inhibition of cell growth by the test compound was calculated assuming the absorption of the control solution as 100%.

Cytotoxicity tests for the other compounds and cell lines were performed following an identical procedure.

Depending on the type of the cell line, the following growth media were used:
the MCF-7 line was grown in Dulbecco's Modified Eagle's Medium (DME) from Sigma (cat. no. D5796),
the HeLa and Hep-G2 lines were grown in PPMI-1640 Medium from Sigma (cat. no. R8758).

$IC_{50}$ values, denoting concentration of a compound needed to obtain 50% inhibition of cell growth, were determined for all the derivatives tested. Derivatives for which $IC_{50} < 4$ μg/mL are generally assumed as active (abbreviated as A), derivatives with values in an IC$_{50}$ range of 4-30 μg/mL are considered medium active (abbreviated as MA), while those for which IC$_{50}$>30 μg/mL are considered non-active (abbreviated as NA).

To enable comparison, identical tests were performed using known cytotoxic agents: 5-fluoro-2'-deoxyuridine and 3'-azido-2',3'-dideoxy-5-fluorouridine.

The results of cytotoxic activity tests for the compound of general formula 1 are shown in Table 2. The values are average results of three independent determinations.

be medium active, approximately comparably potent to 5FdU and comparably active to AddFU. Even though having the lowest activity within the whole series, the other compounds listed in Table 2 are considered medium active.

In a further aspect, the subject matter of the invention is, in particular, the application of 5-fluoro-1-[4-(4-{6-[hydroxy-(6-methoxyquinolin-4-yl)-methyl]-1-aza-bicyclo[2.2.2]oct-3-yl}-[1,2,3]triazol-1-yl)-5-hydroxymethyl-tetrahydro-furan-2-yl]-1H-pyrimidine-2,4-dione with (8S,9R) configuration of the alkaloid moiety (QN5FdU), 5-fluoro-1-

TABLE 2

| | 2 | | 3 | 4 | 5 | 6 | 7 | 8 |
|---|---|---|---|---|---|---|---|---|
| | Cytotoxic activity IC$_{50}$ | | | | | | | |
| 1 | MCF-7 line (breast cancer) | | | HeLa (cervical cancer) | | Hep-G2 (hepatic cancer) | | Calculated partition |
| Compound | [μg/mL] | | [μM] | [μg/mL] | [μM] | [μg/mL] | [μM] | coefficient logP |
| QN5FdU | 0.16 | (A) | 0.27 | 0.16 (A) | 0.27 | 3.8 (A) | 6.40 | 0.40 |
| QD5FdU | 0.98 | (A) | 1.65 | 1.6 (A) | 2.70 | — | — | 0.40 |
| QD5FdU dihydrochloride | 7.00 | (MA) | 10.50 | 8.50 (MA) | 12.75 | — | — | −0.42 |
| CD5FdU | 6.9 | (MA) | 12.24 | 7.0 (MA) | 12.42 | — | — | 0.36 |
| CN5FdU | 7.0 | (MA) | 12.42 | 7.9 (MA) | 14.01 | — | — | 0.36 |
| PQN5FdU | 1.5 | (A) | 2.37 | 2.0 (A) | 3.16 | 6.2 (MA) | 9.78 | 2.16 |
| PQD5FdU | 2.9 | (A) | 4.58 | 2.8 (A) | 4.42 | 6.0 (MA) | 9.47 | 2.16 |
| PQD5FdU dihydrochloride | 4.9 | (MA) | 6.93 | 4.00 (MA) | 5.66 | — | — | 0.35 |
| PCD5FdU | 13.0 | (MA) | 21.54 | 21.4 (MA) | 35.45 | — | — | 2.13 |
| PCN5FdU | 27.2 | (MA) | 45.06 | 27.6 (MA) | 45.72 | — | — | 2.13 |
| 5-fluoro-2'-deoxyuridine | 2.81 | (A) | 11.4 | 3.20 (A) | 13.0 | — | — | −1.72 |
| 3'-azido-2',3'-dideoxy-5-fluorouridine | 2.20 | (A) | 8.11 | 3.0 (A) | 11.06 | 16.0 (MA) | 58.99 | −0.38 |

The cytotoxicity of all the compounds being the subject matter of the application was found as highly or medium active. For four of the eight compounds, the activity tested was higher than that of currently used anti-cancer agents, such as 5-fluoro-2'-deoxyuridine or 3'-azido-2',3'-dideoxy-5-fluorouridine.

In particular, the subject matter of the invention is the application of 5-fluoro-1-[4-(4-{6-[hydroxy-(6-methoxyquinolin-4-yl)-methyl]-1-aza-bicyclo[2.2.2]oct-3-yl}-[1,2,3]triazol-1-yl)-5-hydroxymethyl-tetrahydro-furan-2-yl]-1H-pyrimidine-2,4-dione with (8S,9R) configuration of the alkaloid moiety (QN5FdU), 5-fluoro-1-[4-(4-{6-[hydroxy-(6-methoxyquinolin-4-yl)-methyl]-1-aza-bicyclo[2.2.2]oct-3-yl}-[1,2,3]triazol-1-yl)-5-hydroxymethyl-tetrahydro-furan-2-yl]-1H-pyrimidine-2,4-dione with (8R,9S) configuration of the alkaloid moiety (QD5FdU), 5-fluoro-1-(5-hydroxymethyl-4-{4-[(6-methoxyquinolin-4-yl)-(5-vinyl-1-aza-bicyclo[2.2.2]oct-2-yl)-methoxymethyl]-[1,2,3]triazol-1-yl}-tetrahydrofuran-2-yl)-1H-pyrimidine-2,4-dione with (8S,9R) configuration of the alkaloid moiety (PQN5FdU) and 5-fluoro-1-(5-hydroxymethyl-4-{4-[(6-methoxyquinolin-4-yl)-(5-vinyl-1-aza-bicyclo[2.2.2]oct-2-yl)-methoxymethyl]-[1,2,3]triazol-1-yl}-tetrahydrofuran-2-yl)-1H-pyrimidine-2,4-dione with (8R,9S) configuration of the alkaloid moiety (PQD5FdU) and their pharmaceutically acceptable salts for the manufacture of drugs used in the chemotherapy of breast cancer.

It was confirmed in the tests performed, that QN5FdU (IC$_{50}$=0.16 μg/mL) had the highest activity against breast cancer cells (HeLa line), having more than 17.5-fold higher activity than 5FdU and more than 13-fold higher activity than AddFU. Furthermore, the compounds QD5FdU and PQN5FdU also had very high activity, with the IC$_{50}$ values being in a range of 0.98-1.5 μg/mL, that is, higher than those of 5FdU and AddFU as well. PQD5FdU, in turn, was tested to

[4-(4-{6-[hydroxy-(6-methoxyquinolin-4-yl)-methyl]-1-aza-bicyclo[2.2.2]oct-3-yl}-[1,2,3]triazol-1-yl)-5-hydroxymethyl-tetrahydro-furan-2-yl]-1H-pyrimidine-2,4-dione with (8R,9S) configuration of the alkaloid moiety (QD5FdU), 5-fluoro-1-(5-hydroxymethyl-4-{4-[(6-methoxyquinolin-4-yl)-(5-vinyl-1-aza-bicyclo[2.2.2]oct-2-yl)-methoxymethyl]-[1,2,3]triazol-1-yl}-tetrahydrofuran-2-yl)-1H-pyrimidine-2,4-dione with (8S,9R) configuration of the alkaloid moiety (PQN5FdU) and their pharmaceutically acceptable salts for the manufacture of drugs used in the chemotherapy of cervical cancer.

It was confirmed in the tests performed, that QN5FdU (IC$_{50}$=0.16 μg/mL) had the highest activity against cervical cancer cells (HeLa line), having more than 20-fold higher activity than 5FdU and more than 18-fold higher activity than AddFU. The compounds QD5FdU, PQN5FdU and PQN5FdU had very high activity, with the IC$_{50}$ values being within a range of 1.6-2.8 μg/mL, that is, more than 2 times as high as the activity of 5FdU and slightly higher than that of AddFU. The compounds CD5FdU and CN5FdU were medium active, but less active than 5FdU. Even though having the lowest activity within the whole series, the compounds PCD5FdU and FCN5FdU are considered medium active.

In a further aspect, the subject matter of the invention is in particular the application of 5-fluoro-1-[4-(4-{6-[hydroxy-(6-methoxyquinolin-4-yl)-methyl]-1-aza-bicyclo[2.2.2]oct-3-yl}-[1,2,3]triazol-1-yl)-5-hydroxymethyl-tetrahydro-furan-2-yl]-1H-pyrimidine-2,4-dione with (8S,9R) configuration of the alkaloid moiety (QN5FdU), 5-fluoro-1-[4-(4-{6-[hydroxy-(6-methoxyquinolin-4-yl)-methyl]-1-aza-bicyclo[2.2.2]oct-3-yl}-[1,2,3]triazol-1-yl)-5-hydroxymethyl-tetrahydro-furan-2-yl]-1H-pyrimidine-2,4-dione with (8R,9S) configuration of the alkaloid moiety (QD5FdU), 5-fluoro-1-(5-hydroxymethyl-4-{4-[(6-methoxyquinolin-4-yl)-(5-vinyl-1-aza-bicyclo[2.2.2]oct-2-yl)- methoxymethyl]-[1,2,3]triazol-1-yl}-tetrahydrofuran-2-yl)-1H-pyrimidine-2,4-dione with (8S,9R) configuration of the alkaloid moiety (PQN5FdU) and 5-fluoro-1-(5-hydroxymethyl-4-{4-[(6-methoxyquinolin-4-yl)-(5-vinyl-1-aza-bicyclo[2.2.2]oct-2-yl)-methoxymethyl]-[1,2,3]triazol-1-yl}-tetrahydrofuran-2-yl)-1H-pyrimidine-2,4-dione with (8R,9S) configuration of the alkaloid moiety (PQD5FdU) and their pharmaceutically acceptable salts for the manufacture of drugs used in the chemotherapy of hepatic cancer. It was confirmed in the tests performed that QN5FdU ($IC_{50}$=3.8 μg/mL) had the highest activity against hepatic cancer cells (Hep-G2 line), having 4-fold higher activity man AddFU. The compounds PQN5FdU and PQD5FdU were also highly active, having more than twice as high activity as AddFU.

The cytotoxic activity of the compounds of the invention depends on the absolute configuration of the alkaloid moiety, because the compounds with quinine configuration (8S,9R) have the highest activity.

The other important indicator which determines whether a drug is able to cross lipid biological membranes and thus enables its transport and distribution is the partition coefficient, log P. When the coefficient has a negative value, a drug is excessively polar, water-soluble and unable to penetrate across biological membranes; resulting in its low bioavailability and limited transport. Desired values of the log P partition coefficient for most drugs are within a range of between 2 and 4; for example, average log P values for large collections of drugs and natural products are within a range of 2.2-2.4 (K. Grabowski, G. Schneider, *Curr. Chem. Biol.*, 2007, 1, 115-127; G. Vistoli, A. Pedretti, B. Testa, *Drug Discov. Today* 2008, 13, 285).

5-Fluoro-2'-deoxyuridine and 3'-azido-2',3'-dideoxy-5-fluorouridine have undesirable, negative log P values of −1.72 and 0.38, respectively.

log P partition coefficient values for the compounds of general formula 1 (Table 2) were calculated with commonly used computational algorithms using Dragon software (A. Mauri, V. Consonni, M. Pavan, R. Todesquini, *MATCH Common. Math. Comput. Chem.* 2006, 56, 237-248).

The resulting data (Table 2, column 8) confirmed that the presence of a large alkaloid moiety in the molecules of the compounds of general formula 1 results in a much increased value of the partition coefficient (log P) compared to the reference compounds (5-fluoro-2'-deoxyuridine and 3'-azido-2',3'-dideoxy-5-fluorouridine). In consequence, easier penetration across biological membranes improves transport and distribution. The compounds PQN5FdU and PQD5FdU have particularly favourable partition coefficient values: log P=2.16 which is within a range typical of most drugs.

The subject matter of the invention is explained using certain embodiments which illustrating but not limiting the invention.

In the examples, alkyne derivatives of *cinchona* alkaloids: quinine, quinidine, cinchonine and cinchonidine isolated from *cinchona* bark, were prepared following procedures as reported in the literature. For the derivatives used in the synthesis of compounds QN5FdU, QD5FdU, CD5FdU and CN5FdU, according to K. M. Kacprzak, W. Linder, N. M. Maier, Chiraliry, 2008, 20, 441; for the synthesis of compounds PQN5FdU, PQD5FdU, PQD5FdU and PCN5FdU, according to Patent EP1477488 (2004).

Solvents and other chemical reagents were obtained from Aldrich, Merck and POCh and used as received. Column chromatography was performed on silica gel 60H (0.045-0.075 mm/200-300 mesh) from Merck.

$^1$H NMR, $^{13}$C NMR and $^{19}$F NMR spectra of the compounds were recorded using Varian-Gemini (300 MHz) and Bruker Avance (600 MHz) spectrometers with the following internal standards: tetramethylsilane (TMS) when recording $^1$H NMR and $^{13}$C NMR spectra and trichlorofluoromethane (CFCl$_3$) for $^{19}$F NMR spectra. Mass spectra in ESI technique were recorded using Varian LC-MS instrument.

EXAMPLE 1

Synthesis of 3'-azido-2',3'-dideoxy-5-fluorouridine (AddFU) From 5-fluoro-2'-deoxyuridine A. 2,3'-anhydro-5'-O-benzoyl-5-fluoro-2'-deoxyuridine To a stirred solution of 5-fluoro-2'-deoxyuridine (3.69 g, 15 mmol) and triphenylphosphine (5.90 g, 22.5 mmol) in anhydrous DMF (30 mL) a solution of benzoic acid (2.75 g, 22.5 mmol) and diisopropyl azodicarboxylate (DIAD) (4.43 mL, 22.5 mmol) in anhydrous DMF (7 mL) was added portionwise using a syringe. After 15 min, another portion of DIAD (4.43 mL, 22.5 mmol) and triphenylphosphine (5.90 g, 22.5 mmol) in DMF (7 mL) was added, and the mixture was stirred for another 30 min. Subsequently, the reaction mixture was poured into cooled diethyl ether (370 mL), and the resulting suspension was stirred using a magnetic stirrer for 2 hours. White precipitate of the product was filtered using vacuum and washed with a volume of diethyl ether; this yielded 4.18 g (84%) of 2,3'-anhydro-5'-O-benzoyl-5-fluoro-2'-deoxyuridine which was used without purification in the subsequent stage of synthesis.

$^{13}$C NMR (DMSO-d$_6$) δ: 2.55-2.69 (m, 1H, H-2', H-2"), 3.17 (m, 1H, H-4'), 3.52 (m, 2H, H-5', H-5"), 4.22 (m, 1H, H-3'), 5.08 (pseudo t, 1H, J=6.1 Hz, H-1'), 6.84 (d, 1H, J=3.5 Hz, H-6), 7.52-5.03 (m, 5H, Ph).

$^{13}$C NMR (DMSO-d$_6$) δ: 31.26, 59.38, 77.52, 85.42, 87.34, 125.59 (d, $J_{C-F}$=36.8 Hz), 128.70, 129.13, 130.19, 133.46, 144.27 (d, $J_{C-F}$=248.7 Hz), 151.70, 162.93 (d, $J_{C-F}$=16.3 Hz), 166.84.

$^{19}$F NMR (DMSO-d$_6$) δ: −158.46 (d, 1F, J=5.0 Hz).

MS-ESI m/z: 333 [M+H]$^+$; 355 [M+Na]$^+$; 371 [M+K]$^+$; 331 [M−H]$^−$; 367, 369 [M+Cl]$^−$.

B. 3'-azido-5'-benzoyl-2',3'-dideoxy-5-fluorouridine

To a solution of 2',3'-anhydro-5'-O-benzoyl-5-fluoro-2'-deoxyuridine prepared in step A (3.99 g, 12 mmol) in HMPA (130 mL) lithium azide (1.18 g, 24 mmol) and p-toluenesulphonic acid (monohydrate, 2.28 g, 12 mmol) were added. The stirred solution was healed on an oil bath at 120° C. for 3 hours. After cooling, the reaction mixture was poured into water with ice (1 L), and the product was extracted with ethyl acetate (3×100 mL). Organic extracts were combined and washed with saturated aqueous NaHCO$_3$ solution (50 mL) and water (50 mL), and dried over anhydrous MgSO$_4$. The solvents were removed using a vacuum evaporator, and the crude product was purified using column chromatography on silica gel with a chloroform-methanol mixture (100:1, v/v) as the mobile phase. Yield of 3'-azido-5'-benzoyl-2',3'-dideoxy-5-fluorouridine: 2.93 g, 65%.

$^1$H NMR (DMSO-d$_6$) δ: 2.73-2.89 (m, 1H, H-2', H-2"), 4.12-4.15 (m, 1H, H-4'), 4.46-4.69 (m, 2H, H-5', H-5"), 4.78 (m, 1H, H-3'), 6.18 (pseudo t, 1H, J=6.1 Hz, H-1'), 7.42 (d, 1H, J=3.2 Hz, H-6), 7.49-8.05 (m, 5H, Ph), 11.38 (s, 1H, H-3).

¹³C NMR (DMSO-d₆) δ: 31.26, 59.87, 63.52, 80.51, 83.42, 125.59 (d, $J_{C-F}$=36.8 Hz), 128.75, 129.34, 130.24, 133.58, 144.28 (d, $J_{C-F}$=248.7 Hz), 151.74, 162.94 (d, $J_{C-F}$=16.3 Hz), 166.79.

¹⁹F NMR (DMSO-d₆) δ: −158.46 (d, 1F, J=5.0 Hz).

MS-ESI m/z: 376 [M+H]⁺; 398 [M+Na]⁺; 414 [M+K]⁺; 374 [M−H]⁻; 410, 412 [M+Cl]⁻.

C. 3'-azido-2',3'-dideoxy-5-fluorouridine (AddFU)

3'-Azido-5'-benzoyl-2',3'-dideoxy-5-fluorouridine prepared in step B above (2.5 g) was suspended in methanol saturated with ammonia (200 mL) and stirred using a magnetic stirrer at room temperature for 12 hours. Subsequently, the methanol was removed using a vacuum evaporator, and the solid residue was subjected to column chromatography on silica gel with chloroform-methanol (40:1, v/v) as the mobile phase. Yield of AddFU: 1.64 g, 91%.

¹H NMR (DMSO-d₆)) δ: 2.31-2.45 (m, 1H, H-2', H-2"), 3.69 (m, 1H, H-4'), 3.84 (m, 2H, H-5', H-5"), 4.40 (m, 1H, H-3'), 6.06 (pseudo t, 1H, J=6.1 Hz, H-1'), 8.20 (d, 1H, J=6.8 Hz, H-6), 11.98 (s, 1H, H-3).

¹³C NMR (DMSO-d₆) δ: 36.60, 59.55, 60.42, 84.14, 84.30, 124.60 (d, $J_{C-F}$=34.3 Hz), 141.12 (d, $J_{C-F}$=231.3 Hz), 149.03, 157.25 (d, $J_{C-F}$=26.1 Hz).

¹⁹F NMR (DMSO-d₆) δ: −166.82 (d, 1F, J=7.2 Hz).

MS-ESI m/z: 272 [M+H]⁺; 294 [M+Na]⁺; 310 [M+K]⁺; 270 [M−H]⁻; 306, 308 [M+Cl]⁻.

EXAMPLE 2

Synthesis of Compound QN5FdU

In a round-bottomed flask, AddFU (54 mg; 0.20 mmol) obtained according to Example 1 and on equimolar amount of 10,11-didehydroquinine (64 mg; 0.20 mmol) were placed. The substrates were dissolved in 1,4-dioxane (5 mL) and stirred using a magnetic stirrer at room temperature until dissolved completely. Subsequently, sodium ascorbate (30 mg; 0.15 mmol) and distilled water (1 mL) were added. The mixture was stirred until a homogenous solution was obtained. Finally a 1M CuSO₄ dilution (0.15 mL; 0.14 mmol) was added and the flask was closed with glass stopper. The reaction mixture was vigorously stirred for 24 hours at room temperature. When the reaction was completed, the solvent was removed using a rotary evaporator, and the compound was purified on a chromatographic column with silica gel using a chloroform-methanol mixture (20:1, v/v) as the eluent. Following the chromatographic purification, 5-fluoro-1-[4-(4-{6-[hydroxy-(6-methoxyquinolin-4-yl)-methyl]-1-aza-bicyclo[2.2.2]oct-3-yl}-[1,2,3]triazol-1-yl)-5-hydroxymethyltetrahydrofuran-2-yl]-1H-pyrimidine-2,4-dione with (8S,9R) configuration of the alkaloid moiety (QN5FdU) was obtained with 65% yield.

¹H NMR (400 MHz, DMSO-d₆): δ 1.49 (m, 1H, H-7endo), 1.62 (m, 2H, H-5endo, H-5exo), 1.85 (m, 1H, H-7exo), 2.07 (broad s, 1H, H-4), 2.59-2.79 (m, 3H, H-272", deoxyribose, H-3), 3.15 (m, 3H, H-2endo, H-2exo, H-6exo), 3.40 (m, 2H, H-8, H-6endo), 3.60 (m, 1H, H-5' deoxyribose), 3.70 (m, 1H, H-5" deoxyribose), 3.95 (s, 3H, O—CH₃), 4.20 (m, 1H, H-4' deoxyribose), 5.30 (m, 1H, H-3' deoxyribose), 5.50 (s, 1H, H-9), 5.85 (broad s, 1H, —OH), 6.34 (t, 1H, J=6.2 Hz, H-1' deoxyribose), 7.40 (dd, 1H, J=2.8, 9.2 Hz, H-7'), 7.54 (d, 1H, J=4.6 Hz, H-3'), 7.56 (d, 1H, J=2.5 Hz, H-5'), 7.94 (d, 1H, J=9.2 Hz, H-8'), 8.14 (s, 1H, H-triazole), 8.34 (d, 1H, J=7.1 Hz, 6-H), 8.90 (d, 1H, J=4.2 Hz, H-2').

¹³C NMR (75 MHz, DMSO-d₆): δ 22.87 (C-7), 25.51 (C-5), 26.56 (C-4), 32.27 (C-3), 37.39 (C-2' deoxyribose), 42.06 (C-6), 55.75 (6'-OCH₃), 54.97 (C-2), 58.69 (C-8), 60.12 (C-5' deoxyribose), 60.48 (C-3' deoxyribose), 69.94 (C-9), 84.58 (C-4' deoxyribose), 84.82 (C-1' deoxyribose), 119.23 (C-3'), 121.63 (C-5'), 124.66 (C=CH triazole), 125.12 (C-6'), 126.84 (C-7'), 131.20 (C-8'), 138.54 (C-6, thymidine), 141.59 (C-5 thymidine), 143.92 (C-4'), 147.49 (C=CH triazole), 149.07 (C-2'), 149.85 (C-10'), 157.02 (C-2 thymidine), 157.31 (C-4 thymidine).

¹⁹F NMR (300 MHz, DMSO-d₆): δ −166.542 (d, 1F, J=5.8 Hz).

MS ESI (m/z): (−) 592 (M−H)⁻; 628/630 (M+Cl)⁻; (+) 594 (M+Na)⁺; 632 (M+Ka)⁺; 616 (2M+Na)⁺.

EXAMPLE 3

Synthesis of Compound QD5FdU

Using a procedure identical as in Example 2, a reaction between 54 mg (0.20 mmol) of AddFU and 10,11-didehydroquinidine (64 mg; 0.20 mmol) was performed. Following chromatographic purification, 5-fluoro-1-[4-(4-{6-[hydroxy-(6-methoxyquinolin-4-yl)-methyl]-1-aza-bicyclo[2.2.2]oct-3-yl}-[1,2,3]triazol-1-yl)-5-hydroxymethyltetrahydrofuran-2-yl]-1H-pyrimidine-2,4-dione with (8S,9R) configuration of the alkaloid moiety (QD5FdU) was obtained with 70% yield.

¹H NMR (600 MHz, DMSO-d₆): δ 1.42 (m, 1H, H-7endo), 1.67 (m, 2H, H-5endo, H-5exo), 1.91 (m, 1H, H-7exo), 2.04 (broad s, 1H, H-4), 2.70-2.83 (m, 3H, H-6exo, H-272" deoxyribose), 2.86 (H-6endo), 3.08 (m, 1H, H-3), 3.13 (m, 1H, H-2endo), 3.19 (m, 1H, H-2exo), 3.24 (s, 1H, H-8), 3.72 (m, 1H, H-5" deoxyribose), 3.78 (m, 1H, H-5' deoxyribose), 3.95 (s, 3H, O—CH₃), 4.30 (m, 1H, H-4' deoxyribose), 5.41 (m, 1H, H-3' deoxyribose), 5.66 (s, 1H, H-9), 6.43 (t, 1H, J=6.31 Hz, H-1' deoxyribose), 7.39 (dd, 1H, J=2.69, 9.16 Hz, H-7'), 7.52 (d, 1H, J=4.53 Hz, H-3'), 7.63 (d, 1H, J=2.46 Hz, H-5'), 7.93 (d, 1H, J=9.07 Hz, H-8'), 8.29 (s, 1H, H-triazole), 8.39 (d, 1H, J=6.99 Hz, 6-H), 8.70 (d, 1H, J=4.06 Hz, H-2').

¹³C NMR (150 MHz, DMSO-d₆): δ 22.40 (C-7), 25.13 (C-5), 27.80 (C-4), 32.33 (C-3), 37.44 (C-2' deoxyribose), 47.63 (C-6), 48.74 (C-2), 55.60 (6'-OCH₃), 58.24 (C-8), 60.30 (C-5' deoxyribose), 68.90 (C-9), 69.77 (C-3' deoxyribose), 84.49 (C-4' deoxyribose), 85.11 (C-1' deoxyribose), 102.66 (C-5'), 119.14 (C-3'), 121.21 (C-7'), 121.99 (C=CH triazole), 126.87 (C-6 fluorouridine), 128.19 (C-9'), 131.10 (C-8'), 140.82 (C-5 fluorouridine), 143.87 (C-10', C-4'), 147.43 (C-2'), 148.45 (C=CH triazole), 149.58 (C-2 fluorouridine), 157.00 (C-4 fluorouridine), 157.16 (C-6').

¹⁹F NMR (300 MHz, DMSO-d₆): δ−166.53 (d, IF, J=7.0 Hz, 6-F).

MS ESI (m/z); (−) 592 (M−H); (+) 594 (M+Na)⁺; 616 (2M+Na)⁺.

EXAMPLE 4

Synthesis of Compound CD5FdU

Using a procedure identical as in Example 2, a reaction between 54 mg (0.20 mmol) of AddFU and 10,11-didehydrocinchonidine (58 mg; 0.20 mmol) was performed. Following the chromatographic purification, 5-fluoro-1-(5-hydroxymethyl-4-{4-[(6-hydroxy-quinolin-4-yl-methyl-1-aza-bicyclo[2.2.2]oct-3-yl]-[1,2,3]triazol-1-yl}-tetrahydrofuran-2-yl)-1H-pyrimidine-2,4-dione with (8S,9R) configuration of the alkaloid moiety (CD5FdU) was obtained with 65% yield.

$^1$H NMR (400 MHz, CHCl$_3$-d$_6$): δ 1.29 (m, 1H, H-7endo), 1.95 (m, 2H, H-5endo, H-5exo), 2.3 (m, 1H, H-7exo, H-4), 2.60-3.00 (m, 3H, H-2endo/2exo, H-3), 3.2 (m, 1H, H-8), 3.30-3.90 (m, 6H, H-6exo/6endo, H-575" deoxyribose, H-272" deoxyribose), 4.38 (m, 1H, H-4' deoxyribose), 5.51 (m, 1H, H-3' deoxyribose), 5.62 (broad s, 1H, H-9), 6.49 (t, 1H, J=5.2 Hz, H-1' deoxyribose), 7.70 (m, 2H, H-3', H-6'), 7.86 (m, 1H, H-7'), 8.12 (d, 1H, J=7.2 Hz, H-8'), 8.39 (s, 1H, 6-H), 8.45 (m, 2H, H-triazole, H-5'), 8.96 (s, 1H, H-2').

$^{13}$C NMR (300 MHz, DMSO-d$_6$): δ 18.41 (C-7), 22.65 (C-5), 26.85 (C-4), 30.85 (C-4), 37.50 (C-2' deoxyribose), 47.63 (C-6), 48.41 (C-2), 59.13 (C-5' deoxyribose), 60.66 (C-8), 66.65 (C-9), 72.50 (C-3' deoxyribose), 84.69 (C-4' deoxyribose), 84.92 (C-1' deoxyribose), 118.99 (C-3'), 122.14 (C-7'), 123.62 (C=CH triazole), 125.16 (C-5'), 127.05 (C-6'), 128.29 (C-9'), 129.32 (C-7'), 129.84 (C-8'), 138.59 (C-6 fluorouridine), 146.88 (C-10'), 147.74 (C=CH triazole), 149.10 (C-2'), 157.31 (C-5 fluorouridine), 156.96 (C-2 fluorouridine), 162.37 (C-4 fluorouridine).

$^{19}$F NMR (300 MHz, DMSO-d$_6$): δ -166.50 (d, IF, J=5.8 Hz, 6-F).

MS ESI (m/z): (-) 562 (M-H)$^-$; 598/600 (M+Cl)$^-$; (+) 564 (M+H)$^+$; 686 (M+Na)$^+$, 602 (M+K)$^+$.

EXAMPLE 5

Synthesis of Compound CN5FdU

Using a procedure identical as in Example 2, reaction between 54 mg (0.20 mmol) of AddFU and 10,11-didehydrocinchonine (58 mg; 0.20 mmol) was performed. Following the chromatographic purification, 5-fluoro-1-(5-hydroxymethyl-4-{4-[6-(hydroxy-quinolin-4-yl-methyl)-1-aza-bicyclo[2.2.2]oct-3-yl]-[1,2,3]triazol-1-yl}-tetrahydrofuran-2-yl)-1H-pyrimidine-2,4-dione with (8R,9S) configuration of the alkaloid moiety (CN5FdU) was obtained with 75% yield.

$^1$H NMR (400 MHz, DMSO-d$_6$): δ 1.52 (m, 1H, H-7endo), 1.65 (m, 2H, H-5endo/5exo), 1.80 (m, 1H, H-7exo), 2.05 (broad s, 1H, H-4), 2.60-2.80 (m, 3H, H-272" deoxyribose, H-3), 3.00 (m, 2H, H-2endo, H-6exo), 3.17 (m, 1H, H-2exo), 3.28 (m, 2H, H-8, H-6endo), 3.55 (m, 1H, H-5" deoxyribose), 3.70 (m, 1H, H-5' deoxyribose), 4.19 (m, 1H, H-4' deoxyribose), 5.30 (m, 1H, H-3' deoxyribose), 5.44 (d, 1H, J=5.7 Hz, H-9), 5.86 (broad s, 1H, —OH), 6.35 (t, 1H, J=6.5, 7 Hz, H-1' deoxyribose), 7.58 (d, 1H, J=4.40 Hz, H-3'), 7.63 (t, 1H, J=7.50 Hz, H-6'), 7.75 (t, 1H, J=7.60 Hz, H-7'), 8.03 (d, 1H, J=8.50 Hz, H-8'), 8.15 (s, 1H, 6-H), 8.34 (s, 1H, H-triazole), 8.36 (s, 1H, H-5'), 8.85 (d, 1H, J=4.00 Hz, H-2').

$^{13}$C NMR (400 MHz, DMSO-d$_6$): δ 23.95 (C-7), 26.70 (C-5), 27.42 (C-4), 32.34 (C-3), 37.42 (C-2' deoxyribose), 41.99 (C-6), 48.65 (C-2), 58.68 (C-8), 60.54 (C-9), 70.33 (C-3' deoxyribose, C-5' deoxyribose), 84.58 (C-4' deoxyribose), 84.83 (C-1' deoxyribose), 119.14 (C-3'), 124.15 (C-5'), 124.75, 126.32 (C-6'), 128.90 (C-7', C-9'), 129.76 (C-8'), 138.94 (C-6 fluorouridine), 147.90 (C=CH, triazole, C-10'), 149.08 (C-2'), 150.12 (C-2 fluorouridine), 157.02 (C-5 fluorouridine), 157.28 (C-4 fluorouridine).

$^{19}$F NMR (400 MHz, DMSO-d$_6$): δ -166.62 (d, IF, J=6.1 Hz, 6-F).

MS ESI (m/z): (-) 562 (M-H)$^-$, 598/600 (M+Cl)$^-$; (+) 564 (M+H)$^+$; 686 (M+Na)$^+$, 602 (M+K)$^+$.

EXAMPLE 6

Synthesis of Compound PQN5FdU

In a round-bottomed flask, AddFU (110 mg; 0.40 mmol) obtained as described in Example 1 and an equimolar amount of 9-O-propargylquinine (145 mg; 0.40 mmol) were placed. The substrates were dissolved in methanol (5 mL). Subsequently, sodium ascorbate (60 mg; 0.3 mmol) and distilled water (2 mL) were added. The mixture was stirred until a homogenous solution was obtained. The reaction was initiated by adding 1M of a CuSO$_4$ solution (0.3 mL; 0.3 mmol). The reaction mixture in closed flask was vigorously stirred for 24 hours at room temperature. When the reaction was completed, the solvent was evaporated using a rotary evaporator. Following chromatographic purification on a column with silica gel using a chloroform-methanol (20:1, v/v) mixture as the eluent, 5-fluoro-1-(5-hydroxymethyl-4-{4-[(6-(methoxyquinolin-4-yl)-(5-vinyl-1-aza-bicyclo[2.2.2]oct-2-yl)-methoxymethyl]-[1,2,3]triazol-1-yl}-tetrahydrofuran-2-yl)-1H-pyrimidine-2,4-dione with (8S,9R) configuration of the alkaloid moiety (PQN5FdU) was obtained with 70% yield.

$^1$H NMR (400 MHz, DMSO-d$_6$): δ 1.28 (m, 1H, H-7endo), 1.50 (m, 1H, H-5exo), 1.87 (m, 1H, H-5endo), 1.97 (m, 1H, H-7endo), 2.00 (broad s, 1H, H-4), 2.12 (m, 1H, H-3), 2.70 (m, 2H, H-2" deoxyribose, H-6exo), 2.85 (m, 1H, H-2' deoxyribose), 3.1-3.25 (m, 3H, H-2endo, H-2exo, H-8), 3.55 (m, 1H, H-5" deoxyribose), 3.75 (m, 2H, H-5' deoxyribose, H-6endo), 3.80 (s, 3H, O—CH$_3$), 4.35 (m, 1H, H-4' deoxyribose), 4.65 (m, 2H, O—CH$_2$), 5.02 (d, 1H, J=10.4, Hz, H-11a), 5.12 (d, 1H, J=17.2 Hz, H-11b), 5.44 (m, 1H, H-3' deoxyribose), 5.54 (s, 1H, H-9), 5.85 (m, 1H, H-10), 6.22 (m, 1H, —OH), 6.45 (t, 1H, J=6.3 Hz, H-1' deoxyribose), 7.50 (dd, 1H, J=7.2, 9.3 Hz, H-7'), 7.65 (d, 1H, J=4.6 Hz, H-3'), 7.75 (d, 1H, J=2.3 Hz, 6-H), 8.05 (d, 1H, J=9.3 Hz, H-8'), 8.44 (d, 1H, J=7.2 Hz, H-5'), 8.46 (s, 1H, H-triazole), 8.85 (d, 1H, J=4.6 Hz, H-2'), 11.97 (broad s, 1H, 3-NH).

$^{13}$C NMR (400 MHz, DMSO-d$_6$): δ 18.20 (C-7), 23.83 (C-5), 26.69 (C-4), 36.82 (C-3), 37.53 (C-2' deoxyribose), 42.77 (C-6), 52.90 (C-2), 57.09 (6'-OCH$_3$), 58.45 (C-8), 59.00 (C-3' deoxyribose), 60.56 (C-5' deoxyribose), 61.58 (OCH$_2$), 73.18 (C-9), 84.66 (C-1' deoxyribose), 84.91 (C-4' deoxyribose), 102.17 (C-5 fluorouridine), 116.35 (C-3'), 118.32 (C-11), 122.30 (C-7'), 124.52 (C-5'), 125.07 (C=CH triazole), 126.63 (C-9'), 131.35 (C-8'), 138.84 (C-6 fluorouridine), 138.94 (C-10), 147.40 (C=CH triazole), 149.06 (C-2'), 156.96 (C-6'), 158.06 (C-4 fluorouridine), 174.60 (C-2 fluorouridine).

$^{19}$F NMR (400 MHz, DMSO-d$_6$): δ -166.54 (d, IF, J=6.1 Hz).

MS ESI m/z): (+) 634 (M+Na)$^+$; 672 (M+K)$^+$; 656 (M+Na)$^+$.

EXAMPLE 7

Synthesis of Compound PQD5FdU

Using a procedure identical as in Example 6, reaction between AddFU (110 mg; 0.40 mmol) and 9-O-propargylquinidine (145 mg; 0.40 mmol) was performed. Following chromatographic purification, 5-fluoro-1-(5-hydroxymethyl-4-{4-[(6-methoxyquinolin-4-yl)-(5-vinyl-1-aza-bicyclo[2.2.2]oct-2-yl)-methoxymethyl]-[1,2,3]triazol-1-yl}-tetrahydrofuran-2-yl)-1H-pyrimidine-2,4-dione with (8R, 9S) configuration of the alkaloid moiety (PQD5FdU) was obtained with 75% yield.

¹H NMR (600 MHz, DMSO-d₆): δ 1.28 (m, 1H, H-7endo), 1.36 (m, 1H, H-5endo), 1.63 (m, 1H, H-5exo), 2.02 (m, 1H, H-7exo), 1.80 (s, 1H, H-4), 2.45 (m, 1H, H-3), 2.70 (m, 1H, H-2" deoxyribose), 2.80 (m, 1H, H-2' deoxyribose), 2.34 (H-6exo/6endo), 3.12 (m, 1H, H-2endo), 3.20 (m, 1H, H-2exo), 3.24 (H-8), 3.62 (m, 1H, H-5" deoxyribose), 3.73 (m, 1H, H-5' deoxyribose), 3.99 (s, 3H, O—CH₃), 4.21 (m, 1H, H-4' deoxyribose), 4.55 (m, 2H, O—CH₂), 5.05 (m, 2H, H-11a/11b), 5.39 (m, 1H, H-3' deoxyribose), 5.50 (broad s, 1H, H-9), 5.90 (m, 1H, H-10), 6.40 (t, 1H, J=6.0 Hz, H-1' deoxyribose), 7.44 (m, 1H, H-7'), 7.55 (d, 1H, J=4.5 Hz, H-3'), 7.60 (m, 1H, H-5'), 7.98 (dd, 1H, J=4.8, 9.0 Hz, H-8'), 8.36 (d, 1H, J=7.0 Hz, 6-H), 8.40 (s, 1H, H-triazole), 8.78 (dd, 1H, J=4.6, 10.7 Hz, H-2'), 11.9 (broad s, 1H, 3-NH).

¹³C NMR (150 MHz, DMSO-d₆): δ 19.65 (C-7), 23.49 (C-5), 27.04 (C-4), 36.90 (C-4), 37.45 (C-2' deoxyribose), 47.23 (C-6), 48.36 (C-2), 56.26 (6'-OCH₃), 58.23 (C-8), 58.68 (C-3' deoxyribose), 73.20 (C-9), 60.38 (C-5' deoxyribose), 61.76 (OCH₂), 84.28 (C-1' deoxyribose), 84.71 (C-4' deoxyribose), 102.12 (C-5'), 116.17 (C-11), 118.89 (C-3'), 121.82 (C-7'), 124.08 (C=CH triazole), 124.73 (C-6 fluorouridine), 126.88 (C-9'), 131.25 (C-8'), 138.91 (C-10), 140.78 (C-5 fluorouridine), 144.03 (C-10'), 147.91 (C-2'), (148.99) (C-2 fluorouridine), 149.00 (C=CH triazole), 156.95 (C-6'), 157.80 (C-4 fluorouridine).

¹⁹F NMR (300 MHz, DMSO-d₆): δ −166.55 (d, IF, J=Hz).

MS ESI (m/z): (−) 632 (M−H)⁻; (+) 634 (M+H)⁺; 672 (M+Ka)⁺; 656 (M+Na)⁺.

EXAMPLE 8

Synthesis of Compound PCD5FdU

Using a procedure identical as in Example 6, reaction between AddFU (110 mg; 0.40 mmol) and 9-O-propargylcinchondine (133 mg; 0.40 mmol) was performed. Following chromatographic purification, 5-fluoro-1-(5-hydroxymethyl-4-{4-[quinolin-4-yl)-(5-vinyl-1-aza-bicyclo[2.2.2]oct-2-yl)-methoxymethyl]-[1,2,3]triazol-1-yl}-tetrahydrofuran-2-yl)-1H-pyrimidine-2,4-dione with (8S,9R) configuration of the alkaloid moiety (PCD5FdU) was obtained with 70% yield.

¹H NMR (300 MHz, CHCl₃-d₆): δ 1.23 (m, 1H, H-7endo), 1.49 (m, 3H, H-5endo, H-7exo, H-5exo), 1.70 (s, 1H, H-4), 1.79 (m, 1H, H-3), 2.60-2.80 (m, 4H, H-272" deoxyribose, H-6exo, H-6endo), 3.0-3.2 (m, 2H, H-2endo, H-2exo), 3.42 (H-8), 3.60 (m, 1H, H-5" deoxyribose), 3.75 (m, 1H, H-5' deoxyribose), 4.19 (m, 1H, H-4' deoxyribose), 4.46 (m, 2H, O—CH₂), 5.05 (m, 2H, H-11a/11b), 5.36 (m, 1H, H-3' deoxyribose), 5.45 (s, 1H, H-9), 5.94 (m, 1H, H-10), 6.39 (t, 1H, J=5.4 Hz, H-1' deoxyribose), 7.58 (d, 1H, J=4.4 Hz, H-3'), 7.66 (t, 1H, J=7.3 Hz, H-6'), 7.78 (t, 1H, J=7.3 Hz, H-7'), 7.96 (s, 1H, 6-H), 8.07 (d, 1H, J=8.1 Hz, H-8'), 8.32 (s, 1H, H-triazole), 8.37 (d, 1H, J=7.1 Hz, H-5'), 8.91 (d, 1H, J=3.4 Hz, H-2').

¹³C NMR (75 MHz, DMSO-d₆): δ 23.25 (C-7), 25.35 (C-5), 27.49 (C-4), 35.80 (C-3), 37.48 (C-2' deoxyribose), 47.79 (C-2), 48.84 (C-6), 58.55 (C-3' deoxyribose), 60.15 (C-8), 60.40 (C-5' deoxyribose), 61.88 (OCH₂), 78.17 (C-9), 84.60 (C-4' deoxyribose), 85.03 (C-1' deoxyribose), 114.89 (C-5 fluorouridine), 119.62 (C-3'), 123.91 (C-5'), 124.66 (C=CH triazole), 125.12 (C-11), 126.56 (C-6'), 129.11 (C-7'), 129.81 (C-8'), 140.35 (C-6, fluorouridine, C-10), 143.69 (C-10', C-4'), 147.96 (C=CH triazole), 150.11 (C-2'), 157.27 (C-4 fluorouridine), 162.32 (C-2 fluorouridine).

¹⁹F NMR (300 MHz, DMSO-d₆): δ −166.56 (d, IF, J=7.0 Hz, 6-F).

MS ESI (m/z): (−) 602 (M−H)⁻, 638/640 (M+Cl)⁻; (+) 604 (M+H)⁺, 626 (M+Na)⁺.

EXAMPLE 9

Synthesis of PCN5FdU

Using a procedure identical as in Example 6, reaction between AddFU (110 mg; 0.40 mmol) and 9-O-propargylcinchonine (133 mg; 0.40 mmol) was performed. Following chromatographic purification, 5-fluoro-1-(5-hydroxymethyl-4-{4-[quinolin-4-yl)-(5-vinyl-1-aza-bicyclo[2.2.2]oct-2-yl)-methoxymethyl]-[1,2,3]triazol-1-yl}-tetrahydrofuran-2-yl)-1H-pyrimidine-2,4-dione with (8R,9S) configuration of the alkaloid moiety (PCN5FdU) was obtained with 70% yield.

¹H NMR (400 MHz, DMSO-d₆): δ 1.62 (m, 2H, H-7exo, H-5exo), 1.77 (m, 2H, H-5endo, H-7endo), 1.84 (s, 1H, H-4), 2.43 (m, 1H, H-3), 2.60-2.85 (m, 4H, H-272" deoxyribose, H-6exo, H-6endo), 3.12 (m, 2H, H-2endo, H-2exo), 3.41 (H-8), 3.64 (m, 1H, H-5' deoxyribose), 3.76 (m, 1H, H-5" deoxyribose), 4.18 (m, 1H, H-4' deoxyribose), 4.55 (m, 2H, O—CH₂), 5.00 (dd(AB), 2H, J=9.93, 17.29 Hz, H-11a/11b), 5.35 (m, 1H, H-3' deoxyribose), 5.55 (s, 1H, H-9), 5.79 (m, 1H, H-10), 6.40 (t, 1H, J=6.3 Hz, H-1' deoxyribose), 7.65 (d, 1H, J=4.4 Hz, H-3'), 7.71 (t, 1H, J=7.4 Hz, H-7'), 7.84 (t, 1H, J=7.6 Hz, H-6'), 8.11 (d, 1H, J=8.4 Hz, H-5'), 8.25 (s, 1H, 6-H), 8.34 (s, 1H, H-triazole), 8.36 (s, 1H, H-8'), 8.92 (d, 1H, J=4.6 Hz, H-2').

¹³C NMR (75 MHz, DMSO-d₆): δ 22.14 (C-7), 25.71 (C-5), 27.24 (C-4), 37.93 (C-2' deoxyribose, C-3), 42.86 (C-6), 55.15 (C-2), 59.58 (C-3' deoxyribose), 60.28 (C-8), 61.00 (C-5', deoxyribose), 62.87 (OCH₂), 77.66 (C-9), 85.30 (C-1' deoxyribose, C-4' deoxyribose), 115.71 (C-5 fluorouridine), 119.94 (C-3'), 124.14 (C-11), 124.59 (C-8'), 125.19 (C=CH triazole), 125.65 (C-7'), 126.39 (C-6', C-9'), 127.58 (C-5'), 130.05 (C-6 fluorouridine), 139.04 (C-10), 143.92 (C-4'), 145.54 (C-10), 148.12 (C=CH triazole), 150.64 (C-2'), 157.71 (C-4 fluorouridine), 158.06 (C-2 fluorouridine).

¹⁹F NMR (400 MHz, DMSO-d₆): δ −166.17 (d, 1F, J=6.9 Hz, 6-F).

MS ESI (m/z): (−) 602 (M−H)⁻, 638/640 (M+Cl)⁻, 682/685 (M+Br)⁻; (+) 604 (M+H)⁺, 626 (M+Na)⁺.

EXAMPLE 10

Synthesis of QD5FdU Dihydrochloride

To a round-bottomed flask, QD5FdU (100 mg; 0.16 mmol) and methanol (3 mL) were added, followed by addition of 3 equivalents of HCl as 10% hydrochloric acid solution (0.48 mmol). The solution was stirred at room temperature for 15 minutes; subsequently, the solvents were evaporated in a rotary evaporator on a water bath at 40° C. The dry residue was evaporated twice with additional portion of methanol (3 mL each) to remove excess HCl. 5-fluoro-1-(5-hydroxymethyl-4-{4-[(6-methoxyquinolin-4-yl)-(5-vinyl-1-aza-bicyclo[2.2.2]oct-2-yl)-methoxymethyl]-[1,2,3]triazol-1-yl}-tetrahydrofuran-2-yl)-1H-pyrimidine-2,4-dione dihydrochloride with (8R,9S) configuration of the alkaloid moiety (PQD5FdU) was obtained as pale yellow, solidifying oil with quantitative yield.

MS ESI (m/z): (−) 628 (corresponds to the molecular weight of the product less one chlorine atom, (M−Cl)⁻); (+) 594 (corresponds to the molecular weight of the monoprotonated product less two chlorine atoms, (M+H)⁺); 616 (M+Na)⁺.

EXAMPLE 11

Synthesis of QN5FdU Dihydrochloride

Using a procedure identical as in Example 10, reaction between QN5FdU (100 mg, 0.16 mmol) and HCl (0.48 mmol) was carried out which gave 5-fluoro-1-(5-hydroxymethyl-4-{4-[(6-methoxyquinolin-4-yl)-(5-vinyl-1-aza-bicyclo[2.2.2]oct-2-yl)-methoxymethyl]-[1,2,3]triazol-1-yl}-tetrahydrofuran-2-yl)-1H-pyrimidine-2,4-dione dihydrochloride with (8S,9R) configuration of the alkaloid moiety (PQN5FdU) as pale yellow, solidifying oil with quantitative yield.

MS ESI (m/z): (−) 628 (corresponds to the molecular weight of the product less one chlorine atom, (M−Cl)⁻); (+) 594 (corresponds to the molecular weight of the monoprotonated product less two chlorine atoms, (M+H)⁺); 616 (M+Na)⁺.

EXAMPLE 12

Synthesis of PQD5FdU Dihydrochloride

Using a procedure identical as in Example 10, reaction between PQN5FdU (100 mg, 0.16 mmol) and HCl (0.48 mmol) was carried out which gave 5-fluoro-1-(5-hydroxymethyl-4-{4-[(6-methoxyquinolin-4-yl)-(5-vinyl-1-aza-bicyclo[2.2.2]oct-2-yl)-methoxymethyl]-[1,2,3]triazol-1-yl}-tetrahydrofuran-2-yl)-1H-pyrimidine-2,4-dione dihydrochloride with (8R,9S) configuration of the alkaloid moiety (PQN5FdU) as pale yellow, solidifying oil with quantitative yield.

MS ESI (m/z): (−) 669 (corresponds to the molecular weight of the product less one chlorine atom (M−Cl)⁻); (+) 634 (corresponds to the molecular weight of the monoprotonated product less two chlorine atoms, (M+H)⁺); 656 (M+Na)⁺.

The invention claimed is:

1. 2',3'-Dideoxy-5-fluorouridine derivatives of general formula 1

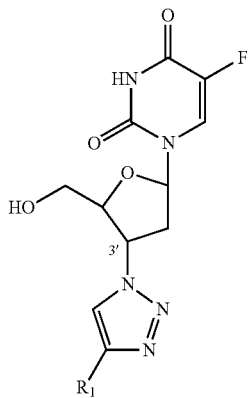

(1)

wherein $R_1$ denotes groups of general formula 2 or 3

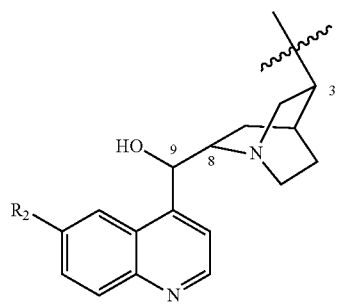

(2)

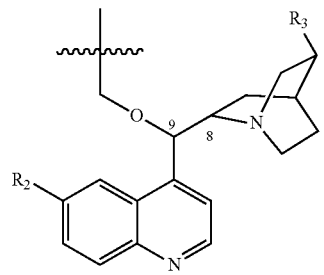

(3)

wherein $R_2$ denotes hydroxy group, H or an alkoxy group containing from 1 to 12 C atoms in a straight or branched chain or a cycloalkyl substituent containing from 3 to 10 C atoms, and $R_3$ denotes vinyl, ethyl or acetylene group.

2. A process for the manufacture of 2',3'-dideoxy-5-fluorouridine derivatives of general formula 1

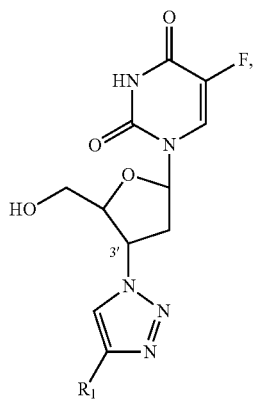

(1)

wherein $R_1$, $R_2$ and $R_3$ are as defined in claim 1, wherein the process comprises a cycloaddition reaction between 3'-azido-2',3'-dideoxy-5-fluorouridine of general formula 11

(11)

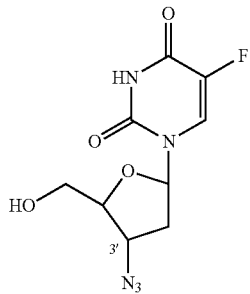

and an appropriate alkyne derivative of *cinchona* alkaloids of general formula 12 or 13,

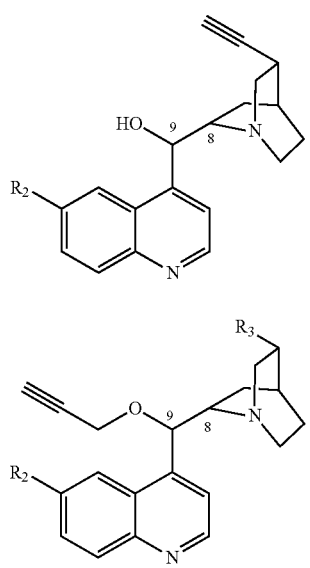

(12)

(13)

wherein $R_2$ and $R_3$ are as defined hereinabove, in the presence of copper(I) ions.

3. Salts of 2',3'-dideoxy-5-fluorouridine derivatives of the general formulae 4, 5 or 6

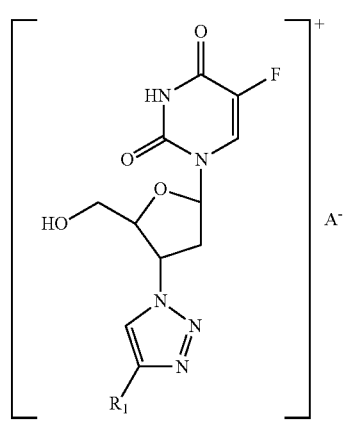

(4)

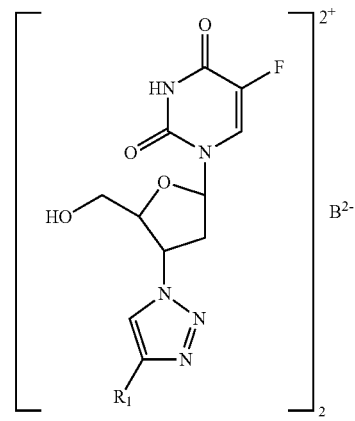

(5)

(6)

wherein:
$A^-$ denotes $Cl^-$, $Br^-$, $I^-$, $NO_3^-$, $HCOO^-$, $CH_3COO^-$, $CH_3SO_3^-$, $CH_3C_6H_4SO_3^-$, $CH_3CH(OH)COO^-$, $HOOC(CHOH)_2COO^-$, $HOOC(CH_2)_2COO^-$, cis-$C_4H_3O_4^-$, $HOCH_2(CHOH)_4COO^-$, trans-$C_4H_3O_4^-$, $C_6H_8O_6^-$, or $C_6H_7O_7^-$,
$B^{2-}$ denotes $SO_4^{2-}$, $HPO_4^{2-}$, $^-OOC(CH_2)_2COO^-$, $^-OOC(CHOH)_2COO^-$, cis-$C_4H_2O_4^{2-}$, or trans-$C_4H_2O_4^{2-}$,
$C^-$ denotes $Cl^-$, $Br^-$, $I^-$, $NO_3^-$, $CH_3SO_3^-$;
$R_1$ denotes monocation of general formula 7 or 8

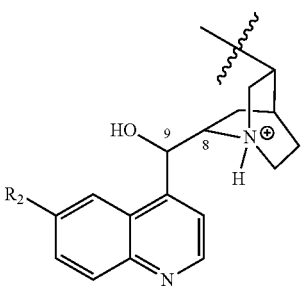

(7)

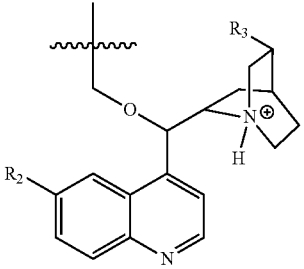

(8)

wherein:
R₂ denotes hydroxy group, H or an alkoxy group containing from 1 to 12 C atoms in a straight or branched chain or a cycloalkyl substituent containing from 3 to 10 C atoms,
Rₐ denotes vinyl, ethyl or acetylene group, and
R₄ is a double protonated dication of general formula 9 or 10,

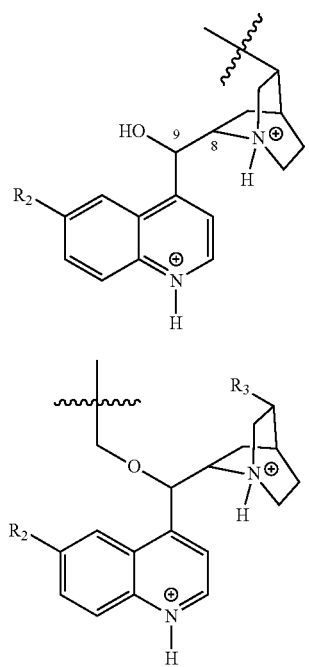

(9)

(10)

wherein:
R₂ and R₃ are as defined above.

4. A method for treating breast cancer, cervical cancer or hepatic cancer, comprising administering to a patient in need of treatment for breast cancer, cervical cancer or hepatic cancer 2',3'-dideoxy-5-fluorouridine derivatives of general formula 1

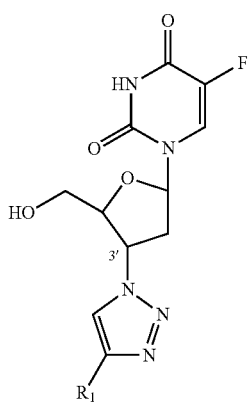

(1)

wherein R₁ denotes the group of general formula 2 or 3

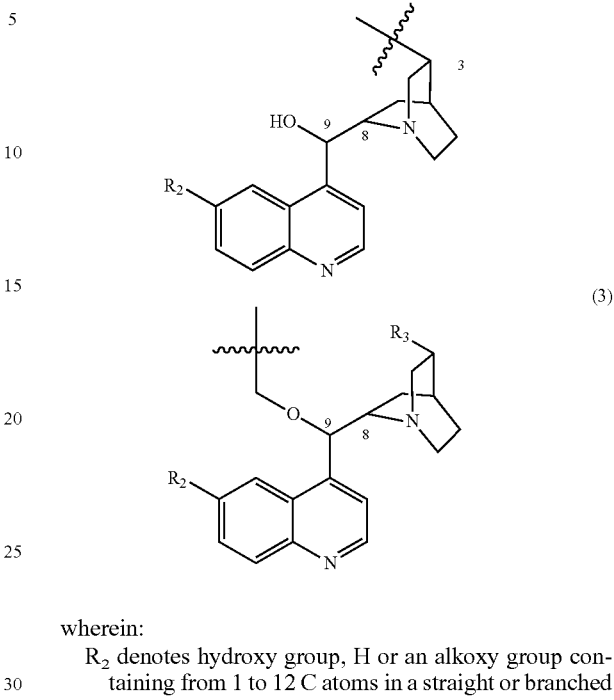

(2)

(3)

wherein:
R₂ denotes hydroxy group, H or an alkoxy group containing from 1 to 12 C atoms in a straight or branched chain or a cycloalkyl substituent containing from 3 to 10 C atoms, and
R₃ denotes vinyl, ethyl or acetylene group
and their pharmaceutically acceptable salts.

5. The method according to claim 4, wherein the method is for treating breast cancer, comprising administering to a patient in need of treatment for breast cancer a formulation comprising a compound selected from the group consisting of 5-fluoro-1-[4-(4-{6-[hydroxy-(6-methoxyquinolin-4-yl)-methyl]-1-aza-bicyclo[2.2.2]oct-3-yl}-[1,2,3]triazol-1-yl)-5-hydroxymethyl-tetrahydro-furan-2-yl]-1H-pyrimidine-2, 4-dione with (8S,9R) configuration of the alkaloid moiety, 5-fluoro-1-[4-(4-{6-[hydroxy-(6-methoxyquinolin-4-yl)-methyl]-1-aza-bicyclo[2.2.2]oct-3-yl}-[1,2,3]triazol-1-yl)-5-hydroxymethyl-tetrahydro-furan-2-yl]-1H-pyrimidine-2,4-dione with (8R,9S) configuration of the alkaloid moiety, 5-fluoro-1-(5-hydroxymethyl-4-{4-[(6-methoxyquinolin-4-yl)-(5-vinyl-1-aza-bicyclo[2.2.2]oct-2-yl)-methoxymethyl]-[1,2,3]triazol-1-yl}-tetrahydrofuran-2-yl)-1H-pyrimidine-2, 4-dione with (8S,9R) configuration of the alkaloid moiety, 5-fluoro-1-(5-hydroxymethyl-4-{4-[(6-methoxyquinolin-4-yl)-(5-vinyl-1-aza-bicyclo[2.2.2]oct-2-yl)-methoxymethyl]-[1,2,3]triazol-1-yl}-tetrahydrofuran-2-yl)-1H-pyrimidine-2, 4-dione with (8R,9S) configuration of the alkaloid moiety, and their pharmaceutically acceptable salts.

6. The method according to claim 4, wherein the method is for treating cervical cancer, comprising administering to a patient in need of treatment for cervical cancer a compound selected from the group consisting of 5-fluoro-1-[4-(4-{6-[hydroxy-(6-methoxyquinolin-4-yl)-methyl]-1-aza-bicyclo[2.2.2]oct-3-yl}-[1,2,3]triazol-1-yl)-5-hydroxymethyl-tetrahydro-furan-2-yl]-1H-pyrimidine-2,4-dione with (8S,9R) configuration of the alkaloid moiety, 5-fluoro-1-[4-(4-{6-[hydroxy-(6-methoxyquinolin-4-yl)-methyl]-1-aza-bicyclo [2.2.2]oct-3-yl}-[1,2,3]triazol-1-yl)-5-hydroxymethyl-tetrahydro-furan-2-yl]-1H-pyrimidine-2,4-dione with (8R,9S) configuration of the alkaloid moiety, 5-fluoro-1-(5-hydroxymethyl-4-{4-[(6-methoxyquinolin-4-yl)-(5-vinyl-1-aza-bicyclo[2.2.2]oct-2-yl)-methoxymethyl]-[1,2,3]triazol-1-yl}-tetrahydrofuran-2-yl)-1H-pyrimidine-2,4-dione with (8S,9R) configuration of the alkaloid moiety, 5-fluoro-1-(5-hydroxymethyl-4-{4-[(6-methoxyquinolin-4-yl)-(5-vinyl-1-aza-bicyclo[2.2.2]oct-2-yl)-methoxymethyl]-[1,2,3]triazol-1-yl}-tetrahydrofuran-2-yl)-1H-pyrimidine-2,4-dione with (8R,9S) configuration of the alkaloid moiety, and their pharmaceutically acceptable salts.

7. The method according to claim 4, wherein the method is for treating hepatic cancer, comprising administering to a patient in need of treatment for hepatic cancer a compound selected from the group consisting of 5-fluoro-1-[4-(4-{6-[hydroxy-(6-methoxyquinolin-4-yl)-methyl]-1-aza-bicyclo[2.2.2]oct-3-yl}-[1,2,3]triazol-1-yl)-5-hydroxymethyl-tetrahydro-furan-2-yl]-1H-pyrimidine-2,4-dione with (8S,9R) configuration of the alkaloid moiety, 5-fluoro-1-[4-(4-{6-[hydroxy-(6-methoxyquinolin-4-yl)-methyl]-1-aza-bicyclo[2.2.2]oct-3-yl}-[1,2,3]triazol-1-yl)-5-hydroxymethyl-tetrahydro-furan-2-yl]-1H-pyrimidine-2,4-dione with (8R,9S) configuration of the alkaloid moiety, 5-fluoro-1-(5-hydroxymethyl-4-{4-[(6-methoxyquinolin-4-yl)-(5-vinyl-1-aza-bicyclo[2.2.2]oct-2-yl)-methoxymethyl]-[1,2,3]triazol-1-yl}-tetrahydrofuran-2-yl)-1H-pyrimidine-2,4-dione with (8S,9R) configuration of the alkaloid moiety, 5-fluoro-1-(5-hydroxymethyl-4-{4-[(6-methoxyquinolin-4-yl)-(5-vinyl-1-aza-bicyclo[2.2.2]oct-2-yl)-methoxymethyl]-[1,2,3]triazol-1-yl}-tetrahydrofuran-2-yl)-1H-pyrimidine-2,4-dione with (8R,9S) configuration of the alkaloid moiety, and their pharmaceutically acceptable salts.

8. The 2',3'-Dideoxy-5-fluorouridine derivatives according to claim 1, wherein $R_2$ denotes methoxy group.

9. The process according to claim 2, wherein $R_2$ denotes methoxy group.

10. The salts according to claim 3, wherein $R_2$ denotes methoxy group.

11. The method according to claim 4, wherein $R_2$ denotes methoxy group.

* * * * *